United States Patent [19]
Hellstrom et al.

[11] Patent Number: 5,185,432
[45] Date of Patent: Feb. 9, 1993

[54] MONOCLONAL ANTIBODIES AND ANTIGEN FOR HUMAN NON-SMALL CELL LUNG CARCINOMA AND OTHER CERTAIN HUMAN CARCINOMAS

[75] Inventors: Karl E. Hellstrom; Joseph P. Brown; Ingegerd Hellstrom, all of Seattle; Hans Marquardt, Mercer Island, all of Wash.

[73] Assignee: Oncogen, Seattle, Wash.

[21] Appl. No.: 834,172

[22] Filed: Feb. 26, 1986

[51] Int. Cl.$^5$ .............. C07K 15/28; C12P 21/08; C12N 5/20
[52] U.S. Cl. .............. 530/388.8; 530/391.3; 435/240.27; 424/1.1
[58] Field of Search .............. 435/68, 240.26, 240.24, 435/240.27; 530/387, 388.8, 391.3; 424/1.1

[56] References Cited

U.S. PATENT DOCUMENTS 4,737,579  4/1988  Hellstrom et al. .............. 530/384

FOREIGN PATENT DOCUMENTS 125928  11/1984  European Pat. Off. .
8602735  5/1986  World Int. Prop. O. .

OTHER PUBLICATIONS

Varki et al., "Antigens Associated with a Human Lung Adenocarcinoma Defined by Monoclonal Antibodies", Cancer Research, V.44, 681–687, 1984.
Sikora et al., "Human Monoclonal Antibodies to Lung-Cancer Antigens" British J. Cancer (1981) V.43, 696–700.
Bergh et al., "Surface-Glycoprotein Patterns of Established Human Lung Cancer Cell Lines and Primary Cultures", Anticancer Research, (1985) V.5, 323–328.
Wofsy et al., "Modification and Use of Antibodies to Label Cell Surface Antigens" Selected Methods in Cellular Immunology, Mishell et al., Editors, W. H. Freeman and Company, San Francisco, pp. 287–304, 1980.
Hellstrom et al., "Monoclonal Mouse Antibodies Raised Against Human Lung Carcinoma", Cancer Research, V.46, 3917–3923, Aug. 1986.
Cole et al., 1985, In Monoclonal Antibodies and Cancer Therapy (Alan Liss, Inc.) pp. 77–96.
Crawford et al., 1983, J. Gen. Virol. 64:697–700.
Seigneurin et al., 1983, Science 221:173–175.
Rosen et al., 1983, J. Immunol, 130:2899–2900.
Monjour et al., 1983, Lancet 1337–1338.
Hirohashi et al., 1982, Gann 73:345–347.
Chiorazzi et al., 1982, J. Exp. Med. 156:930–935.
Kazbor et al., 1982, Hybridoma 1:200.
Steinitz et al., 1981, Immunol. Today, pp. 38–39.
Warenius et al., 1983, Eur. J. Clin. Oncol. 19:347–355.
Olsson et al., 1983, J. Immunol. Methods 61:17–32.
Bischoff et al., 1982, FEBS Letters 147:64–68.
Croce et al., Nature 288:488–489.
Teng et al., 1983, Proc. Natl. Acad. Sci. U.S.A. 80:7308–7312.
Butler et al., 1982, Clin. Res. 30(2):344A.
Yarmush et al., 1980, Proc. Natl. Acad. Sci. U.S.A. 77:2899–2903.
McKearn et al., 1979, Immunol. Rev. 47:92–115.

Primary Examiner—David L. Lacey
Assistant Examiner—George C. Elliott
Attorney, Agent, or Firm—Pennie & Edmonds

[57] ABSTRACT

The present invention is concerned with novel monoclonal antibodies which bind strongly to a protein antigen associated with human non-small cell lung carcinomas ("NSCLC") human small cell lung carcinomas and certain other human carcinomas including many carcinomas of the colon and breast. The antibodies bind to normal human cells to a much lesser degree than to tumor cells. The antibodies find use both in diagnostic methods such as the detection of malignant cells associated with NSCLC and in therapeutic methods for treatment of human in NSCLC and certain other human carcinomas. Also disclosed is a novel 110,000 dalton glycoprotein antigen found on the cell surface of human non-small lung carcinoma tumor cells and on cells from certain other human cancers. The amino terminal amino acid sequence of this antigen is:

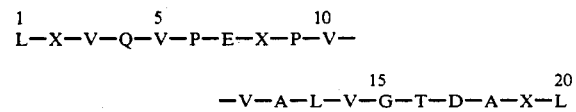

in which X represents an unidentified amino acid.

18 Claims, No Drawings

MONOCLONAL ANTIBODIES AND ANTIGEN FOR HUMAN NON-SMALL CELL LUNG CARCINOMA AND OTHER CERTAIN HUMAN CARCINOMAS

TABLE OF CONTENTS

1. Field of the Invention
2. Background of the Invention
   2.1. Human Lung Carcinoma
   2.2. Monoclonal Antibodies
   2.3. Monoclonal Antibodies and Antigens Associated with Lung Cancer
3. Summary of the Invention
4. Description of the invention
   4.1. Methods for Producing Monoclonal Antibodies Against NSCLC
      4.1.1. Fusion Techniques
      4.1.2. EBV-Transformation Techniques
      4.1.3. EBV-Hybridoma Techniques
      4.1.4. Cell Propagation and Antibody Production
   4.2. Monoclonal Antibodies
      4.2.1. Antigen Recognized by Monoclonal Antibodies
   4.3. Uses for Monoclonal Antibodies Against Human NSCLC
      4.3.1. Diagnostic Applications
      4.3.2. Therapeutic Applications
   4.4. Diagnostic Kits Examples
   5.1. Preparation of Monoclonal Antibodies
   5.2. Characterization of the L20 Monoclonal Antibody
      5.2.1. Detection of Binding of L20 to Cultured Cells
      5.2.2. Isotype Determination of L20 Antibody
   5.3. Antigen Recognized by L20 Antibody
   5.4. In Vitro Immunohistological Application

1. FIELD OF THE INVENTION

The present invention relates to a novel monoclonal antibody, and to methods for production and use of such novel monoclonal antibody specific for carcinoma antigens. More specifically the monoclonal antibody of this invention is immunospecific for and/or immunoreactive with a protein antigen associated with human non-small cell lung carcinoma (NSCLC) and certain other human carcinomas including some carcinomas of the breast, colon, etc.

The monoclonal antibody of the present invention is reactive with a determinant of a glycoprotein antigen associated with NSCLC cells and also with other carcinomas including breast, colon and small cell lung carcinomas. The monoclonal antibody of this invention possesses distinctive characteristics and capabilities which makes such antibody suitable for both in vivo and in vitro clinical diagnostic purposes. Additionally the antibody of the present invention is suited for therapeutic uses. For example, the novel antibody can be used as a target-selective carrier of various agents which have anti-tumor effects including, but not limited to: chemotherapeutic drugs, toxins, immunological response modifiers, and radioisotopes. Moreover, the hybridomas which produce such antibody can be modified using recombinant DNA technology so that the resulting antibodies can mediate antibody-dependent cellular cytotoxicity or can be cytolytic to tumor cells in the presence of complement components.

2. BACKGROUND OF THE INVENTION

2.1. Human Lung Carcinoma

Lung carcinomas are responsible for the majority of deaths from cancer among men and are overtaking breast carcinomas as the most frequent cause of cancer death among women. This disease can be divided into four major histological types: (1) epidermoid or squamous (30%), (2) adenocarcinoma (35%), (3) large-cell undifferentiated (15%), and (4) small-cell (20%). The term non-small cell lung carcinoma ("NSCLC") includes the following cell types: epidermoid carcinoma cells, adenocarcinoma cells, and large undifferentiated carcinoma cells.

Most cases of lung carcinomas are incurable by chemotherapy and radiation therapy. Small cell lung carcinomas may respond to chemotherapy and radiation therapy by a reduction in size, but this does not afford a total cure. Complete surgical removal of the tumor appears to be the only effective therapy. Unfortunately, however, fewer than 30% of lung cancer patients have tumors which can be totally resected at diagnosis. Of these, fewer than one-third survive 5 years after apparent complete surgical removal of the tumor. There is a great need, therefore, for methods that would make possible an earlier diagnosis of lung cancer, a better definition of the degree of cancer spread, and a more effective therapy.

2.2. Monoclonal Antibodies

Monoclonal antibodies representing homogeneous antibody molecules which bind to a single molecular site (i.e. an epitope) on an antigen with a specific binding or affinity constant are prepared by three methods known in the art.

Monoclonal antibodies may be prepared by hybridoma techniques devised by Kohler and Milstein (1975, Nature 256:495; 1976, Eur. J. Immunol. 6:511). By fusing antibody-producing cells (splenic lymphocytes) with myeloma cells, Kohler and Milstein created hybrid cells that gave rise to immortal cell lines possessing both the ability to produce antibody and the ability to grow permanently in cell culture. The hybridomas secrete a single type of immunoglobulin of predefined antigenic specificity depending upon the antigen to which the lymphocytes have previously been exposed.

Alternatively, monoclonal antibodies may be produced by in vitro transformation of mammalian peripheral blood B lymphocytes, for example, with Epstein Barr virus (EBV). The virus immortalizes the antibody-producing lymphocytes. Techniques for such transformation are known in the art (see, for example, Steinmetz et al., 1977, Nature 269:420; Crawford et al., 1983, The Lancet, i:386).

Finally, monoclonal antibodies may be produced using techniques that combine both the EBV-immortalization and cell fusion or hybridoma technology. Cole et al. (1985, in Monoclonal Antibodies and Cancer Therapy, Alan Liss, Inc., pp. 77–96) describe techniques for fusing a human plasmacytoma or lymphoblastoid cell line fusion partner with EBV-transformed donor lymphocytes which previously have been established as a cell line. In such system, both parental cell lines are immortal. Hence, the fusion partner must have appropriate drug markers to counter-select against the parental lines when the fused hybridoma is cultured. The resulting EBV-hybridomas produce antibodies with specificity of the EBV-lymphocyte cell line employed.

Monoclonal antibodies can be made in large quantities by in vitro cell culture of particular hybridoma or transformed cell lines. Additionally, inoculation of a hybridoma cell line into the peritoneal cavity of compatible mammals such as mice results in a tumor that secretes high concentrations (1 to 20 mg/ml) of monoclonal antibody into the tumor ascites fluid. By removing the ascites fluid and purifying the monoclonal antibody, a single mouse may provide sufficient antibody for use in thousands of diagnostic assays.

2.3. Monoclonal Antibodies and Antigens Associated with Lung Cancer

Monoclonal antibodies to human lung cancer antigens have been described by Sikora et al., 1981, Brit. J. Cancer 43:696; Cuttita et al., 1981, Proc. Nat'l Acad. Sci. USA 78:4591; Moody et al., 1981, Science 214:1246; Minna et al., 1981, In Vitro 17:1058; Kennel et al., 1981, Cancer Res. 41:3465; Chem. Abst. 95(15):1308502; Baylin et al., 1982, Proc. Nat'l Acad. Sci. USA 79:4650; Carney et al., 1982, Pathobiology Annual 12:115; Gazdar et al., 1983, Seminars in Oncology 10:3; Hollinshead et al., 1983, Cancer Detect. Prevent 6:185; Mulshine et al; 1983, J. Immunol. 131:497; Huang et al., 1983, Arch. Biochem. Biophys. 220:318; Saji et al., 1984, Hybridoma 3:119; Bio. Abst. 79005569; Bosslet et al., Behring. Inst. Mitt. 74:27; Chem. Abst. AC101(9): 706686; Roset et al., 1984, Cancer Res. 44:2052; Bio. Ast. 79023605; Princler et al., 1982, Cancer Res. 42:843; Mazauric et al., 1982, Cancer Res. 42:150; Braatz et al., 1982, Cancer Res. 42:849; Sobel et al., 1982, Fed. Proc. 41:409, Cole et al., 1985 in Monoclonal Antibodies and Cancer Therapy, Alan Liss, Inc., pp. 77–96; and Varki et al., 1985, in Monoclonal Antibodies and Cancer Therapy, Alan Liss, Inc., p. 207.

U.S. patent applications Ser. Nos. 667,521, now abandoned, filed on Nov. 2, 1984 and 785,177 filed on Oct. 7, 1985 and applications Ser. Nos. 684,759, now U.S. Pat. No. 6,122,293, filed on Dec, 21, 1984 and 776,321, now U.S. Pat. No. 4,906,562, filed on Oct. 18, 1985 and application Ser. No. 738,612, now U.S. Pat. No. 4,873,188, filed on May 28, 1985 disclose certain monoclonal antibodies against human non-small cell lung carcinoma.

Monoclonal antibodies may be used for methods that would make possible an earlier diagnosis of lung cancer, a better definition of the spread of the cancer, and more effective methods for therapy of lung cancer. A prerequisite, however, is to find antibodies to antigens that are more strongly expressed in lung cancer than in normal adult tissues. In view of the known heterogeneity of tumor cell populations, the presence of several determinants on the same antigen molecule, the anticipated differences between antigens with respect to their stability as diagnostic markers and therapeutic targets, and the different biological characteristics of different antibodies to the same antigen, a number of different antibodies to a number of different antigens may be needed.

3. SUMMARY OF THE INVENTION

The present invention is concerned with a novel class of monoclonal antibody, illustrated by L20, which is specific for a determinant site on a glycoprotein antigen associated with human non-small cell lung carcinoma (NSCLC) cells. The term "NSCLC cells" includes epidermoid carcinoma cells, adenocarcinoma cells and large cell undifferentiated carcinoma cells. The determinant site can also be found on antigens of some other carcinomas, e.g., some carcinomas of the breast and colon and small cell lung carcinoma. Thus, the antibody of the invention will also bind to cells from other carcinomas and be useful for the diagnosis and therapy of all other tumors expressing the antigen identified by antibody L20. The present monoclonal antibody binds to a much lesser degree to noral adult cells than to tumor cells. The term "binds to a much lesser degree" means that the binding will not be detectable at all, or will be detectable only as a very weak staining when immunohistological techniques are employed. Thus, the antibody has a high degree of specificity for antigen characteristic of NSCLC and certain other carcinomas.

The invention also comprises the novel L20 antigen identified by antibody L20 and the class of antibodies that bind to, are immunospecific for or immunoreactive with this antigen. Further encompassed are methods for using the purified or cloned L20 antigen as a vaccine to immunize against certain carcinomas.

The present invention also concerns certain diagnostic methods employing the monoclonal antibody of the invention. For instance, the antibody may be used in methods for determining the presence of the malignant condition in human lung tissue and other human tissues. The methods involve examining the tissue for the presence of an antigen having the characteristics of a 110,000 dalton glycoprotein defined by antibody L20. For example, the tissue can be contacted with an antibody which defines a determinant site on a cell associated antigen having the characteristics of the antigen defined by antibody L20, a functional equivalent or a fragment of this antibody and any interactions of said antibody and antigenic determinants are detected. One such method involves the determination of the presence of NSCLC cells in a specimen suspected of containing such cells. The specimen is contacted with the monoclonal antibody, which is capable of distinguishing such cells from other cell types which may be present in the specimen. The contact is carried out under conditions for binding of the antibody to such cells. After contact, the presence or absence of binding of the antibody to the cells in the specimen is determined. This binding is related to the presence or absence of the NSCLC cells in the specimen. Generally, the specimen is contacted with a labeled specific binding partner of the monoclonal antibody. This label is capable of producing a detectable signal.

Another diagnostic method involves the in vivo localization of a tumor by administering to a patient a purified antibody or antibody fragment of the present invention labelled with an agent which gives a detectable signal. The localization is then detected using external scintography, emission tomography or radionuclear scanning. This method can also provide better ways to stage cancer patients with respect to extent of disease and to monitor changes in response to therapy.

The invention also has therapeutic applications, since the L20 antibody and similar antibodies can react with the L20 antigen that is expressed in high concentrations at the tumor cell surface. Antibodies can, therefore, be used as carriers of various agents which have an antitumor effect, including, but not restricted to, chemotherapeutic drugs, toxins, immunological response modifiers, and radioisotopes.

Furthermore, the L20 antibody may be modified so that it can mediate antibody dependent cellular cytotoxicity (ADCC), that is, that it can kill NSCLC cells in the presence of human lymphocytes or macrophages or that it becomes cytolytic to tumor cells in the presence of human complement. Such modification can be accomplished for example by techniques recently developed for the production of "chimeric antibodies." Accordingly, genes coding for the variable region of the L20 antibody molecule are spliced together with human genes coding for the Fc region of an antibody with appropriate biological activity (such as the ability to activate human complement and mediate ADCC). Novel antibodies of mouse or human origin, can be also made to the L20 antigen having the appropriate biological functions.

4. DESCRIPTION OF THE INVENTION

The present invention concerns a novel monoclonal antibody, designated L20, which is immunospecific for and/or immunoreactive with an antigen on human NSCLC cells and cells from several other human carcinomas, including carcinoma of the colon and breast and small cell lung carcinoma, methods for producing such novel monoclonal antibody and certain diagnostic and therapeutic methods employing the antibody.

The invention further concerns a novel cell surface antigen characteristic of human NSCLC and certain other human carcinomas of the breast, colon and lung and methods for using such novel antigen.

4.1. Methods for Producing Monoclonal Antibody Against NSCLC

Monoclonal antibodies against human NSCLC and certain other human carcinomas can be prepared by hybridoma fusion techniques, by EBV-transformation of human antibody-producing lymphocytes, or by techniques that combine cell fusion and EBV-immortalization technologies.

4.1.1. Fusion Techniques

According to one embodiment of the present invention, monoclonal antibodies against NSCLC are prepared using hybridoma cell fusion techniques. For example, human lung carcinoma cells from pleural effusions, cultured cells from explanted human NSCLC tumors, or cells from a normal fetal lung or lysates from such cells are used as the immunogen. In one illustrative example, explanted cells from a NSCLC, human lung adenocarcinoma #3082 were used as the immunogen (see Section 5.1.). The cells are injected, for example, into a mouse and, after a sufficient time, the mouse is sacrificed and somatic antibody-producing lymphocytes are obtained. Antibody-producing cells may be derived from the lymph nodes, spleens and peripheral blood of primed animals. Spleen cells are preferred. Mouse lymphocytes give a higher percentage of stable fusions with the mouse myelomas described below. The use of rat, rabbit and frog somatic cells is also possible. The spleen cell chromosomes encoding desired immunoglobulins are immortalized by fusing the spleen cells with myeloma cells, generally in the presence of polyethylene glycol. Several myeloma cell lines may be used for producing fused cell hybrids, including NSI-Ag4/1, X63-Ag8, MPC11-45.6TG1.7, X63-Ag.653, Sp2/0-Ag14, Fo, and S194/5XX0.Bu.1, derived from mice, and 210.RCY3.Ag1.2.3, U-226AR and GM1500GTGAL2 derived from rats, (Hammerling, et al., 1981, "Monoclonal Antibodies and T-cell hybridomas" in Research Monographs in Immunology, Vol. 3, J. L. Turk, ed; Elsevier/North Holland Biomedical Press. New York). In one illustrative example, NS1 cells were used (see Section 5.1.) The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various conventional methods exist for isolation and purification of the monoclonal antibodies, so as to free them from other proteins and other contaminants.

4.1.2. EBV-Transformation Techniques

According to an alternative embodiment of the present invention, monoclonal antibodies against NSCLC are prepared using EBV-transformation techniques. For example lymphocytes derived from peripheral blood, tumor-draining lymph nodes, bone marrow aspirates, tumors or pleural effusions from patients with NSCLC are immortalized using EBV according to methods devised by Cole et al., 1984, Cancer Res. 44:2750. As noted by Cole et al., B lymphocytes specific for tumor antigens are rare in lung cancer patients. Hence it is particularly important to enhance the number of lymphocytes producing antibody by pre-selecting lymphocytes producing antibody against the relevant antigen. Thus the EBV-transformation techniques involves two steps: (1) enrichment of cells with receptors for the given antigen, i.e. L20 antigen described in Section 4.2., and (2) immortalization of such cells by infection with EBV.

4.1.3. EBV-Hybridoma Techniques

According to another alternative embodiment of the present invention, monoclonal antibodies against NSCLC are prepared using a combination of EBV-transformation and hybridoma fusion techniques such as described by Cole et al., 1985, in Monoclonal Antibodies and Cancer Therapy, Alan R. Liss, Inc; pp. 77–96. For example, a myeloma cell line is fused with donor lymphocytes from NSCLC patients which have been previously transformed by EBV and established as a cell line capable of growing and developing in culture conditions. In order to be able to select the resulting EBV-hybridoma fusion cell lines, it is necessary that the fusion partner possess dominant appropriate selectable drug markers such as ouabain or neomycin resistance so that parental cells do not develop when culturing the fused hybridoma cell lines. A suitable line is the thioguanine resistant GM-150, ouabain resistant lymphoblastoid cell line, KR-4 described by Cole et al., supra. The resulting hybridomas are cloned by conventional techniques.

4.1.4. Cell Propagation and Antibody Production

Once the desired fused cell hybrids or transformed cell lines have been selected and cloned into individual antibody-producing cell lines, each cell line may be propagated in either of two conventional manners. The individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. As discussed by Cole et al., supra, when human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies (see Cole et al., supra).

4.2. Monoclonal Antibodies

The antibody of the present invention binds to a novel cell surface glycoprotein antigen, designated L20 antigen, characteristic of human NSCLC cells and cells from certain other human carcinomas (see Section 4.2.1.). The glycoprotein antigen has a molecular weight of about 110,000 daltons when subjected to immunoprecipitation on polyacrylamide gel electrophoresis (see Section 5.3). Digestion of the L20 antigen with glycanase showed that it contains N-linked oligosaccharide chains.

As an illustrative example of the present invention, L20 antibody is produced by the L20 murine hybridoma described in Section 5.1. The L20 antibody is of the IgG1 isotype and (see Section 5.2.2.) has an avidity of approximately $3 \times 10^8$. It does not bind detectably to normal cells, such as fibroblasts, endothelial cells, or epithelial cells in the major organs. By "does not bind detectably" is meant that only a very weak staining or no staining at all is detected by immunohistology.

Also included within the scope of the invention are useful binding fragments of the above monoclonal antibody, such as Fab, F(ab')2, Fv fragments etc. The antibody fragments are obtained by conventional techniques. For example, useful binding fragments may be prepared by peptidase digestion of the antibody using papain or pepsin.

Similar antibodies, including antibodies of different isotypes, different affinities, and novel biological functions, such as the ability to kill tumor cells in the presence of complement or effector cells such as lymphocytes or macrophages, are also within the scope of the invention. While the above specific example of the novel antibody of the invention is directed to an antibody binding to a specific determinant site on the respective antigen and being of the IgG1 subclass from a murine source, this is not meant to be a limitation. The above antibody and those antibodies having functional equivalency with the above antibody whether from a murine source, other mammalian source including human, or other sources, or combinations thereof are included within the scope of this invention, as well as antibodies of other isotypes. By the term "functional equivalency" is meant that the antibody is capable of binding to the above-described determinant site and capable of competing with a particular antibody of the invention for such site. That is, such antibody, when combined with a specimen containing a cell or cell fragment having such determinant site, will bind to such determinant site and will block an antibody of the invention from binding to such site. Furthermore, since the antigen of the invention can have more than one determinant site, the invention includes monoclonal antibodies which define determinant sites other than determinant sites defined by the aforementioned monoclonal antibody and which can be identified by sequential immunoprecipitation assays, known in the art.

The invention also includes antibodies prepared in response to antigen binding sites, or idiotypes of the L20 antibody, since such anti-idiotypic antibodies may be used to analyze the immune response to tumor antigens for diagnostic purposes and for inducing immune responses for therapeutic or prophylactic purposes (Nepom et al., 1984, Proc. Nat'l Acad. Sci. 81:2664).

4.2.1. L 20 Antigen Recognized by Monoclonal Antibodies

The antigen recognized by the monoclonal antibodies of the present invention comprises a novel cell surface glycoprotein antigen characteristic of NSCLC cells, and certain other carcinomas including breast, colon and small cell lung carcinoma. The antigen has a molecular weight of about 110,000 daltons.

The amino terminal amino acid sequence of the novel glycoprotein antigen is as follows:

$$\begin{array}{c} 1 \quad\quad\quad 5 \quad\quad\quad 10 \\ L-X-V-Q-V-P-E-X-P-V- \end{array}$$

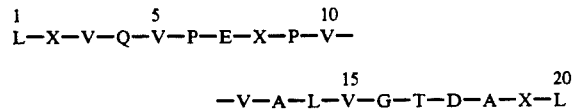

in which X represents an amino acid that has not been identified as yet, and the rest of the letters represent the conventional single letter abbreviations for amino acids. A comparison of this sequence with those stored in the current protein data base (PIR Release 6.0, November 1985) reveals no significant sequence homology with any other known sequences.

4.3. Uses for Monoclonal Antibodies and the L20 Antigen

4.3.1. Diagnostic Applications

The monoclonal antibodies of this invention can be used as probes in detecting discrete antigens in human NSCLC and other human tumors. One method of the invention involves the determination of the presence of a malignant condition in lung tissue and other human tissues by examining the tissue for the expression or lack of expression of a glycoprotein antigen having the characteristics of the L20 antigen. The term "having the characteristic of" means that the antigen is reactive with an antibody which recognizes the L20 antigen. The expression or lack of expression of this antigen can provide clinically exploitable information which is not available with standard histopathological techniques.

Monoclonal antibodies of the invention can be used, for example, to detect non-small cell lung carcinoma cells in histological and cytological specimens. For instance, using the immunoperoxidase staining technique described in Section 5.4., excised tissue specimens of adenocarcinoma, epidermoid and small cell carcinoma of the lung exhibited intense positive staining. Normal lung, spleen, breast, colon, kidney, liver, brain, heart, skin, thyroid, testis, vagina and normal lymphocytes were negative.

Another important in vitro diagnostic application of the monoclonal antibodies of this invention is the evaluation of carcinomas other than the NSCLC. The antibody has been used to detect the epitope in carcinomas of the breast, colon and in small cell lung carcinoma. Normal samples of these tissues did not express the determinant. Thus, the monoclonal antibody is useful for detecting an antigenic determinant in these carcinomas which is tumor-associated. Hence the monoclonal antibody may be a useful diagnostic reagent for breast and colon carcinoma and for small cell lung carcinoma.

Alternatively, immunofluorescent techniques can be used to examine human tissue specimens with the monoclonal antibodies of the present invention. In a typical protocol, slides containing cryostat sections of frozen, unfixed tissue biopsy or excised tumor samples or cytological smears are air dried and incubated with the monoclonal antibody in a humidified chamber at room temperature. The cytological smears include exfoliative cell specimens. By the term "exfoliative" is meant that the specimen comprises isolated cells or clumps of cells obtained by scraping or washing the surface of tissue, which cells are removed individually or in scales or laminae. The exfoliative cell specimen is to be distinguished from excised tissue such as that obtained at biopsy. The method may find utility in the detection of a malignant condition in exfoliative cell specimens from the lung such as a sputum sample, from the bronchus, gastro-intestinal tract including oral pharynx, mouth, a cervical smear etc.

After drying, the slides are layered with a preparation of antibody against the monoclonal antibody, usually some type of antimouse immunoglobulin if the monoclonal antibody used is derived from fusion of a mouse spleen lymphocyte and a mouse myeloma line. This antimouse immunoglobulin is conjugated using known techniques with a compound such as rhodamine or fluorescein isothiocyanate that fluorescences at a particular wavelength. The staining pattern and intensities within the sample are then determined by fluorescent light microscopy and optionally photographically recorded.

The above description is directed primarily to the use of the antibodies of the invention in immunofluorescence techniques. However, the antibodies of the invention can be used in most assays involving antigen-antibody reactions. The assays may be homogeneous or heterogenous. In a homogeneous assay the specimen may be a tissue lysed and clarified to remove debris. The immunological reaction usually involves the specific antibody, a label analyte, and the sample of interest. The signal arising from the label is modified, directly or indirectly, upon the binding of the antibody to the labeled analyte. Both the immunological reaction and detection of the extent thereof are carried out in a homogenous solution. Immunochemical labels which may be employed include free radicals, fluorescent dyes, enzymes, bacteriophages, coenzymes, and so forth.

In a heterogeneous assay approach, the reagents are usually the specimen, the specific antibody, and a means for producing a detectable signal. The monoclonal antibody is usually coated on a solid support or solid-phase. The specimen in a liquid phase is then contacted with the antibody in the solid-phase. The solid-phase support is then separated from the liquid phase and either the solid-phase or the liquid phase is examined for a detectable signal employing means for producing such signal. The signal is related to the presence of the analyte in the specimen. Means for producing a detectable signal include the use of radioactive labels, fluorescers, enzymes, and so forth. Examples of heterogenous immunoassays are the radioimmunoassay, immunofluorescence methods, enzyme-linked immunoassays, and the like.

For a more detailed discussion of the above immunoassay techniques, see "Enzyme-Immunoassay," by Edward T. Maggio, 1980, CRC Press, Inc., Boca Raton, Fla. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

The antibodies of the invention can also be employed for in vivo diagnostic applications. For example, antibodies or fragments prepared from antibodies, e.g. Fab and F(ab')$_2$ fragments can be used to image tumors, including metastatic deposits in human patients with NSCLC in a manner analogous to that described for malignant melanoma in Larson et al., 1983, J. Nucl. Med. 24:123 and in Larson et al., 1983, J. Clin. Invest., 72:2101. The purified antibody or fragments thereof are labelled with an agent giving a detectable signal, for example, a radioisotope such as $^{131}$I and administered in a suitable carrier, for example, intraveneously, to a patient. The localization of the tumor-bound antibody is detected by external scintography, emission tomography or radionuclear scanning, using e.g., a gamma camera.

4.3.2. Therapeutic Applications

The antibodies of the invention may also be used therapeutically. The monoclonal antibodies can be used in conjunction with a broad spectrum of pharmaceutical or cytotoxic agents. For example, an antibody can be bound to a toxin to form an immunotoxin (Jansen et al., 1982, Immunol. Rev. 62:185) or to a radioactive material e.g.; $^{125}$I, $^{131}$I, etc. (Order, 1984, Compr. Ther. 10:9; Larson et al., 1983, J. Clin. Invest. 72:2101; Carrasquillo et al., 1984, Cancer Treatment Reports, 68:317) or to a drug (Rowland et al., 1985, Cancer Immunol. Immunother. 19:1) to form a radiopharmaceutical or pharmaceutical. Conjugated antibodies can be administered to patients to achieve enhanced tumoricidal effects through the cytotoxic action of the chemotherapeutic agent delivered to the tumor based on the binding affinity of the antibody moiety.

So-called "chimeric antibody" molecules of the antibody of the present invention may be prepared containing a mouse antigen-binding domain with human constant region domains (Morrison et al., 1984, Proc. Nat'l Acad. Sci. U.S.A. 81: 6851; Takeda et al., 1985, Nature, 314:452) and this approach may be used to construct novel antibody molecules with desirable effector functions such as the ability to activate human complement and mediate ADCC (Neuberger et al., 1984, Nature 312:604).

Another therapeutic use of the monoclonal antibodies of the present invention is to prepare anti-idiotypic antibody using the L20 antibody as the immunogen (see, for example, Nepom et al., 1984, Proc. Nat'l Acad. Sci. U.S.A., 81: 2864; Lee et al., 1985, Proc. Nat'l Acad. Sci. 82:6286).

An attractive aspect of the present invention is that the present antibodies can be combined with other antibodies to NSCLC or other tumors, such as those disclosed in the U.S. patent applications Ser. No. 667,521, now abandoned, filed Nov. 2, 1984, Ser. No. 684,759, now U.S. Pat. No. 5,122,293, filed Dec. 21, 1984, and Ser. No. 738,612, now U.S. Pat. No. 4,873,188, filed May 28, 1985. The combination is effective in detecting the types of non-small cell lung carcinomas mentioned above, namely large cell undifferentiated lung carcinoma, adenocarcinoma, and epidermoid carcinoma.

The monoclonal antibodies of the invention also define determinant sites on an antigen associated with other carcinomas such as breast carcinomas, colon carcinomas and small cell lung carcinoma (see Section 5. Table 1). Consequently, the present antibodies can find use in therapeutic methods and therapeutic products directed to such carcinomas.

The novel antigen of the present invention, referred to as antigen L20 may also be used for therapeutic applications. The antigen can be purified from tumors or produced by recombinant DNA technology (Brown et al., copending U.S. patent application Ser. No. 827,313, now abandoned, filed on Feb. 7, 1986, incorporated by reference herein). The gene coding for the L20 antigen may be cloned by methods which first enrich the mRNA of the L20 antigen. By one such method, polysomes (consisting of mRNA, ribosomes and nascent polypeptide chains) can be purified by immunoaffinity chromatography with antibody that recognizes the L20 antigenic determinant on the nascent chain. The mRNA is isolated by immunoprecipitation with e.g. L20 antibody and the cDNA is cloned in an appropriate expression vector. Alternatively, L20 antibody or antiserum to L20 antigen might be used to screen a cDNA library using an expression vector. The purified or cloned L20 antigen may be administered alone as an immunogen or together with a proper immunological adjuvant. Alternatively, the gene coding for the antigen may be inserted into the gene for a virus, such as the vaccinia virus, to produce a recombinant DNA product to be used as the immunogen (Brown et al., copending U.S. patent application Ser. No. 827,313, now abandoned filed on Feb. 7, 1986).

4.4. Diagnostic Kits

The invention also encompasses diagnostic kits for carrying out the methods disclosed above. In one embodiment, the diagnostic kit comprises (a) a monoclonal antibody more specifically defined above and (b) a conjugate of a specific binding partner for the monoclonal antibody and a label capable of producing a detectable signal. The reagents may also include ancillary agents such as buffering agents and protein stabilizing agents, e.g., polysaccharides and the like. The diagnostic kit may further comprise, where necessary, other components of the signal-producing system including agents for reducing background interference, control reagents, an apparatus for conducting a test, etc. In another embodiment, the diagnostic kit comprises a conjugate of a monoclonal antibody of the invention and a label capable of producing a detectable signal. Ancillary agents as mentioned above may also be present.

5. EXAMPLES

The invention is further demonstrated by the following non-limiting illustrative Examples.

5.1. Preparation of Monoclonal Antibodies

Monoclonal antibodies were produced using hybridoma fusion techniques described previously by Yeh et al., 1979, Int. J. Cancer 29:299. A three month-old Balb/c mouse was immunized using explanted cultured cells from a human adenocarcinoma of the lung designated 3082 as the immunogen. The mouse received four intraperitoneal injections of approximately $10^7$ cells. Three days after the last immunization, its spleen was removed, suspended in culture medium and fused with NS1 mouse myeloma cells (Kohler and Milstein, supra). The mixture was seeded to form low density cultures originating from single fused cells (clones).

Supernatants from hybrid cells were screened for direct binding activity on lung cancer cell lines using both an ELISA assay and an autoradiographic indirect $^{125}I$-labelled protein A assay (Brown et al., 1979, J. Immunol. Meth., 31: 201). Extracts of cell membranes from the tumor used for immunization were prepared using a procedure modified from Colcher et al., 1981, Cancer Res. 42: 1451; Yeh et al., supra. Tissues were washed with PBS and cells from intact tumors were suspended by pressing through a stainless steel screen. After this, 1 mM $NaHCO_2$ containing 1 mM phenylemethylsulfonylfluoride (Calbiochem-Behring Corp., San Diego, Calif.) was added, and the material was then homogenized on ice, with 50 strokes of the B pestle of a Dounce homogenizer. After centrifugation for 15 min at $27,000 \times g$, the supernatant was removed, and the pellet was resuspended in PBS, sonicated for 1 min, and stored at $-70°$ C.

Hybridomas which produced antibodies binding to the cell membrane extracts were cloned, expanded in vitro, and further tested for antibody specificity. Those hybridomas which produced antibody of apparent specificity for human lung cancer were recloned, expanded, and injected into pristaneprimed 3-month old BALB/c mice, where they grew as ascites tumors.

Following this procedure, hybridoma cell line L20 was obtained, cloned and injected into mice to develop as an ascites tumor. Antibody secreted into the ascites was purified on protein A Separose (Ey et al., 1978, Immunochemistry, 15:429) or by gel filtration in Sephacryl S-300. Purified antibody was used for further characterization.

5.2. Characterization of the L20 Monoclonal Antibody

5.2.1. Detection and Binding of L20 to Cultured Cells

The subcellular localization of antigen was determined by measuring antibody binding to cells before or after permeabilization with non-ionic detergent. Antibodies binding to the cell surface of intact cultured cells were identified either by direct binding assays with $^{125}I$-labelled antibody (Brown et al., 1981, Proc. Nat'l Acad. Sci. U.S.A., 78: 539) or by indirect fluorescence using the fluorescence activated cell sorter (FACS) II. Antibodies binding to intracellular locations were determined by direct binding of $^{125}I$-labelled antibody to cells following fixation with paraformaldehyde and subsequent permeabilization with the non-ionic detergent NP-40.

For binding assays performed by using radiolabelled antibodies (Brown et al., supra), cultured cells ($10^6$) were incubated on ice for 30 min with $10^6$ cpm of $^{125}I$-labelled antibody in 100 μl of binding buffer. The suspension was layered onto 0.2 ml dinonylphtalate: dibutylphtalate (1:1 v/v) and centrifuged. The pellet and the aqueous phase were counted for $^{125}I$. To measure non-specific binding, parallel incubations were performed with unlabelled antibody as a competitor (Brown et al., supra).

TABLE I

| BINDING OF RADIOIODINATED L20 ANTIBODY TO CULTURED CELLS | |
|---|---|
| CELLS | SPECIFIC BINDING |
| Calu-1 lung adenocarcinoma | 45,400 |

TABLE I-continued
BINDING OF RADIOIODINATED L20 ANTIBODY TO CULTURED CELLS

| CELLS | SPECIFIC BINDING |
| --- | --- |
| H3082 lung adenocarcinoma | 50,100 |
| H2981 lung adenocarcinoma | 64,100 |
| H2984 lung adenocarcinoma | 119,300 |
| MCF7 breast carcinoma | 78,800 |
| 3017 melanoma | 2,200 |
| Normal T cells | 200 |
| Jurkat T leukemia | 200 |
| Daudi B lymphoma | 200 |

5.2.2. Isotype Determination of L20 Antibody

To determine the class of immunoglobulins produced by the L20 hybridoma cell line, the following techniques were utilized:

(a) Ouchterlony immunodiffusion.

An aliquot of supernatant of particular hybridoma cells was placed into the center well of a 25% agar plate. Monospecific rabbit anti-mouse Ig isotypes antibodies (Southern Biotechnology, Birmingham, Ala.) were placed in the outer wells and the plate was incubated for 2 hr at room temperature and overnight at 4° C.

(b) ELISA isotyping.

Dynatech Immuolon 96-well plates were coated with each antiserum at 1 µg/ml concentration, 50 µl/well in PBS and left covered overnight at 4° C. The plates were washed with PBS/Tween 20, 0.05% and blocked with medium 100 µl/well for 1 hr at room temperature. After washing the plates, supernatants from the L20 hybridoma were added and incubated at room temperature for 1 hr. After washing with PBS, bovine serum albumin (BSA) plates were incubated at 37° C. for 2 hr with monospecific rabbit anti-mouse Ig isotype antibodies coupled to peroxidase (Zymed). After washing, plates were incubated with 1 mg/ml orthophenylendiamine and 0.03% $H_2O_2$ in 0.1M citrate buffer pH 4.5. Optical density at 630 nm was determined on a Dynatec ELISA plate reader.

The L20 monoclonal antibody is of the $IgG_1$ isotype.

5.3. Antigen Recognized by L20 Antibody

In order to identify protein antigens, lung carcinoma cells were surface radioiodinated or metabolically labelled with $^{35}$S-methionine. Antigens were isolated from cell lysates by incubation with monoclonal antibody, addition of goat anti-mouse IgG, and adsorption to Staphylococcus aureus. Immune precipitates were washed and subjected to preparative sodium dodecyl-sulfate polyacrylamide gel electrophoresis (SDS-PAGE) on a 10-20% acrylamide gel. Following electrophoresis, the gel was stained with Coomassie Brilliant Blue (0.5% by weight to 10% acetic acid and 30% isopropanol) and destained in a solution of acetic acid (5%, v:v) and methanol (17%, v:v). The stained L20 antigen band was excised with a razor blade and immediately subjected to electroelution with a ECU-040 Electroelutor/Concentrator (C.B.S. Scientific Co., San Diego, Calif.) according to methods described by Hunkapiller et al., 1983, Methods in Enzymol. 91: 227-236.

Automated Edman degradation was performed with approximately 23 pmol of L20 antigen (based on the yield of identified L-1) in a gas-phase sequencer (Model 470A, Applied Biosystems, Inc., Foster City, Calif.). The phenylthiohydatoin amino acid derivatives were analyzed by reverse-phase high performance liquid chromatography (HPLC) using a Model 120A on-line HPLC unit (Applied Biosystems, Inc.) with a PTH-C18 column (2.1×220 mm, Applied Biosystems, Inc.) and a sodium acetate/tetrahydrofuran/acetonitrile gradient for elution.

The amino terminal amino acid sequence is as follows:

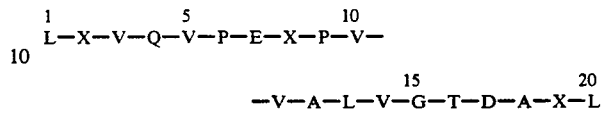

in which X represents an amino acid that has not been identified.

Comparison of this sequence with those stored in the current protein data base (PIR Release 6.0, Nov. 1985), did not reveal any significant sequence homology with any other known sequence.

The antigen recognized by L20 antibody is a glycoprotein antigen of about 110,000 daltons molecular weight.

5.4. In Vitro Immunohistological Application

The unlabeled antibody technique of Sternberger, 1979, in Immunochemistry, John Wiley & Sons, New York, pp: 104-169, as modified by Garrigues et al., 1982, Int. J. Cancer 29: 511, was used for immunohistological studies on frozen sections. The target tissues for these tests were obtained at surgery and frozen within 4 hr of removal in isopentane, precooled in liquid nitrogen. Tissues were then stored in liquid nitrogen or at −70° C. until use. Rabbit anti-mouse IgG (Sternberger-Meyer Immunochemicals, Inc., Jarettsville, Md.) was used at a dilution of 1/50. Mouse peroxidase-antiperoxidase complexes (PAP, Sternberger-Meyer Immunochemicals, Inc.) containing 2 mg/ml of specifically purified PAP was used at a dilution of 1/80. Frozen sections were prepared, dried, treated with acetone and dried (Garrigues et al., supra). Sections to be used for histologic evaluation were stained with hematoxylin. To decrease non-specific backgrounds, sections were preincubated with normal human serum diluted 1/5 (Garrigues et al., supra). Mouse antibodies, goat anti-mouse IgG, and mouse PAP were diluted in a solution of 10% normal human serum and 3% rabbit serum.

The staining procedure consisted of treating serial sections with either specific or control antibody for 2.5 hr, incubating for 30 min with rabbit anti-mouse IgG diluted 1/50 and exposing to mouse PAP complex diluted 1/80 for 30 min. After each treatment with antibody, the slides were washed twice in PBS. The immunohistochemical reaction was developed with freshly prepared 0.5% 3,3'-diaminobenzidine tetrahydrochloride (Sigma, St. Louis, Mo.) and 0.01% $H_2O_2$ in 0.05M Tris buffer, pH 7.6 for 8 min. Further exposure to a 1% $OsO_4$ solution in distilled water for 20 min intensified the stain. The sections were rinsed with water, dehydrated in alcohol, cleared in xylene, and mounted on slides.

The slides were each evaluated under code and coded samples were checked by an independent investigator. Typical slides were photographed by using differential interference contrast optics (Zeiss-Nomarski). The degree of antibody staining was evaluated as 0 (no reactivity), +(a few weakly positive cells), + +(at least one third of the cells positive),+ + +(most cells positive),++++(approximately all cells strongly positive). Since differences between + and 0 staining were less clear cut than between + and + + staining, a staining graded as + + or greater was considered "positive". Both neoplastic and stroma cells were observed in tumor samples. The staining recorded is that of the tumor cells, since the stroma cells were not stained at all, or were stained much more weakly than the tumor cells.

TABLE II

IMMUNOPEROXIDASE STAINING OF TUMORS AND NORMAL TISSUE SPECIMENS WITH L20 MONOCLONAL ANTIBODY

| TISSUE TYPE | NUMBER POSITIVE/NUMBER TESTED* |
|---|---|
| Lung carcinoma: | |
| adenocarcinoma | 18/20 |
| epidermoid | 3/3 |
| bronchial | 0/1 |
| small cell | 4/4 |
| Lung carcinoma: cell lines | 3/3 |
| Breast carcinoma | 4/7 |
| Colon carcinoma | 5/8 |
| Melanoma | 5/8 |
| Renal carcinoma | 1/1 |
| Liposarcoma | 0/1 |
| Normal lung | weak staining of 1 of 3 samples tested |
| Normal spleen | negative |
| Normal breast | negative |
| Normal colon | negative |
| Normal kidney | negative |
| Normal liver | negative |
| Normal brain | negative |
| Normal heart | negative |
| Normal skin | negative |
| Normal thyroid | negative |
| Normal testis | negative |
| Normal vagina | negative |
| Normal lymphocyte pellet | negative |

All specimens examined were frozen sections of tissues obtained at surgery. See text for detailed description of immunohistological methods. A staining of 2+ (representing at least one third of cells positive) was considered as positive.

It is apparent that many modifications and variations of this invention as set forth above may be made without departing from the spirit and scope. The specific embodiments described are given by way of example only and the invention is limited only by the terms of the appended claims.

A cell line, L20, as described herein has been deposited with the American Type Tissue Culture Collection, Rockville, Md., and has been assigned accession number ATCC No. HB8913. The invention described and claimed herein is not to be limited in scope by the cell line deposited since the deposited embodiment is intended as a single illustration of one aspect of the invention and any equivalent monoclonal cell lives which produce a functionally equivalent monoclonal antibody are within the scope of this invention. In fact, various modifications of the invention in addition to those shown and described herein will become apparent to those skilled in the art from the foregoing description. Such modifications are intended to fall within the scope of the appended claims.

What is claimed is:

1. A monoclonal antibody, the antigen-combining site of which binds to a protein antigen having a molecular weight of about 110,000 daltons and an amino terminal amino acid sequence as follows:

```
1           5              10
L—X—V—Q—V—P—E—X—P—V—

15              20
—V—A—L—V—G—T—D—A—X—L
``` in which X represents an unidentified amino acid, which protein antigen is a cell surface determinant of human non-small cell lung carcinoma.

2. The monoclonal antibody of claim 1 which comprises an IgG isotype.

3. The monoclonal antibody of claim 1 which comprises an IgG1 isotype.

4. The monoclonal antibody of claim 1 which is produced by a murine hybridoma cell line.

5. The monoclonal antibody of claim 4 in which the murine hybridoma comprises a hybridoma having the characteristics of HB 8913 as deposited with the A.T.C.C.

6. The monoclonal antibody of claim 4 or an Fab, F(ab')2, or Fv fragment thereof, in which the hybridoma, HB8913 is formed by fusing a NS1 mouse myeloma cell with a mouse splenocyte obtained from a Balb/c mouse immunized with cells containing a 110 kd protein antigen, as determined by polyacrylamide gel electrophoresis, in which the protein antigen has an amino terminal amino acid sequence as follows:

```
1           5              10
L—X—V—Q—V—P—E—X—P—V—

15              20
—V—A—L—V—G—T—D—A—X—L
``` in which X represents an unidentified amino acid, which protein antigen is a cell surface determinant of human non-small cell lung carcinoma.

7. A Fab, F(ab')2 or Fv fragment of the monoclonal antibody of claim 1.

8. The fragment of the monoclonal antibody of claim 7 conjugated to a label capable of producing a detectable signal.

9. The fragment of the monoclonal antibody of claim 8 in which the label comprises a fluorescer, a radiolabel, a chromophore or an enzyme.

10. The monoclonal antibody of claim 1 conjugated to a label capable of producing a detectable signal.

11. The monoclonal antibody of claim 10 in which the label comprises a fluorescer, a radiolabel, a chromophore or an enzyme.

12. A monoclonal antibody, the antigen combining site of which competitively inhibits the immunospecific binding of monoclonal antibody L20 produced by hybridoma HB8913, as deposited with the ATCC, to its target protein antigen, which protein antigen is a cell surface determinant of human non-small cell lung carcinoma.

13. The monoclonal antibody of claim 12 conjugated to a label capable of producing a detectable signal.

14. The monoclonal antibody of claim 13 in which the label comprises a fluorescer, radiolabel, a chromophore, or an enzyme.

15. A Fab, F(ab')2 or Fv fragment of the monoclonal antibody of claim 12.

16. The fragment of the monoclonal antibody of claim 15 as conjugated to a label capable of producing a detectable signal.

17. The fragment of the monoclonal antibody of claim 16 in which the label comprises a fluorescer, a radiolabel, a chromophore, or an enzyme.

18. Hybridoma cell line HB8913 as deposited with the ATCC.

* * * * *